United States Patent [19]
Mandell

[11] Patent Number: 5,435,722
[45] Date of Patent: Jul. 25, 1995

[54] DENTAL BUR WITH LIQUID-COOLED TIP

[76] Inventor: Charles S. Mandell, 3220 Stirling Rd., Hollywood, Fla. 33021

[21] Appl. No.: 215,157

[22] Filed: Mar. 21, 1994

[51] Int. Cl.⁶ .............................................. A61C 3/02
[52] U.S. Cl. .................................................. 433/165
[58] Field of Search .............. 433/82, 104, 165, 166; 408/57, 59; 51/356

[56] References Cited

U.S. PATENT DOCUMENTS

| | | | |
|---|---|---|---|
| 2,799,934 | 7/1957 | Kern | 433/82 |
| 3,393,452 | 7/1968 | Nelson | 433/166 |
| 3,971,135 | 7/1976 | Leu | 433/165 |
| 4,058,898 | 11/1977 | Nash | 433/166 |
| 4,284,406 | 8/1981 | Hughes | 433/165 |
| 4,526,542 | 7/1985 | Kochis | 433/165 |
| 4,601,661 | 7/1986 | Du Bé et al. | 433/134 |
| 4,681,541 | 7/1987 | Snaper | 433/165 |
| 4,795,292 | 1/1989 | Dye | 408/59 |
| 4,897,037 | 1/1990 | Appleby | 433/166 |
| 4,950,108 | 8/1990 | Roos | 408/59 |
| 5,100,322 | 3/1992 | Weissman | 433/165 |

*Primary Examiner*—O'Connor Cary E.
*Attorney, Agent, or Firm*—Oltman and Flynn

[57] ABSTRACT

According to the invention, there is provided an elongated liquid-cooled dental bur having a long direction, a proximal part adapted to be inserted into a drive device connected with a source of cooling fluid, a distal part having a cutting tip, a first channel in the proximal part fluidly communicating with the source of cooling fluid and at least one orifice extending from the first channel directed at the cutting tip for directing a spray of cooling liquid at the cutting tip, and further including a collar radially extending from the proximal part having a circumference, wherein the orifice is disposed in the collar proximal to the circumference, and wherein the collar has an end surface disposed transversely to the long direction facing the distal part, and the orifice is disposed in the end surface. The distal part is preferably removably secured to the collar, for removal and replacement of worn cutting tips. The distal part preferably fits into an axial bore in the collar and is secured in the axial bore with a set screw. The cutting tip may be substantially spherically shaped.

15 Claims, 2 Drawing Sheets

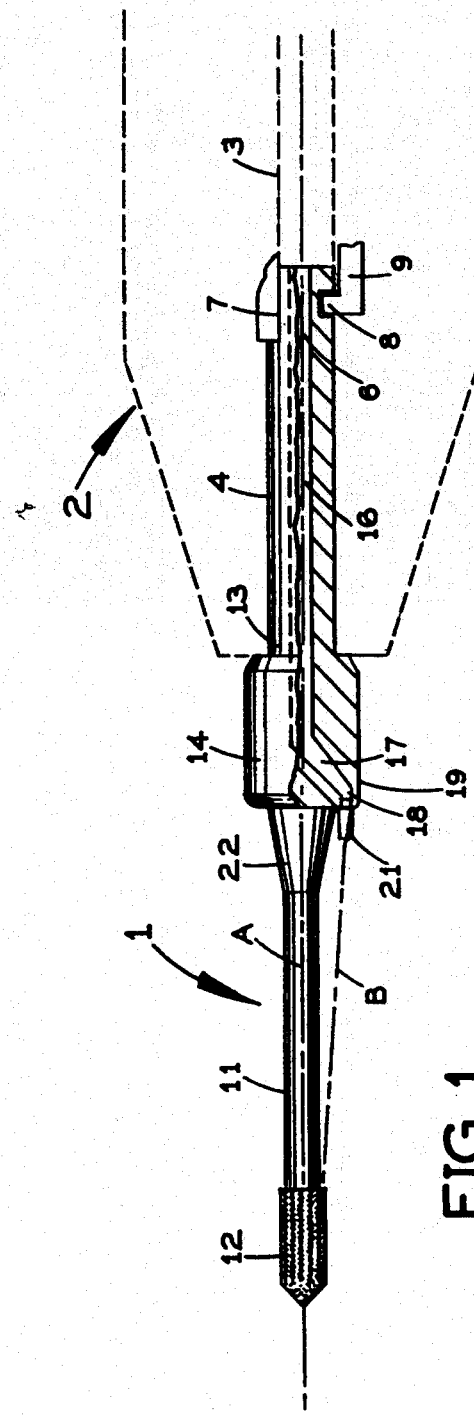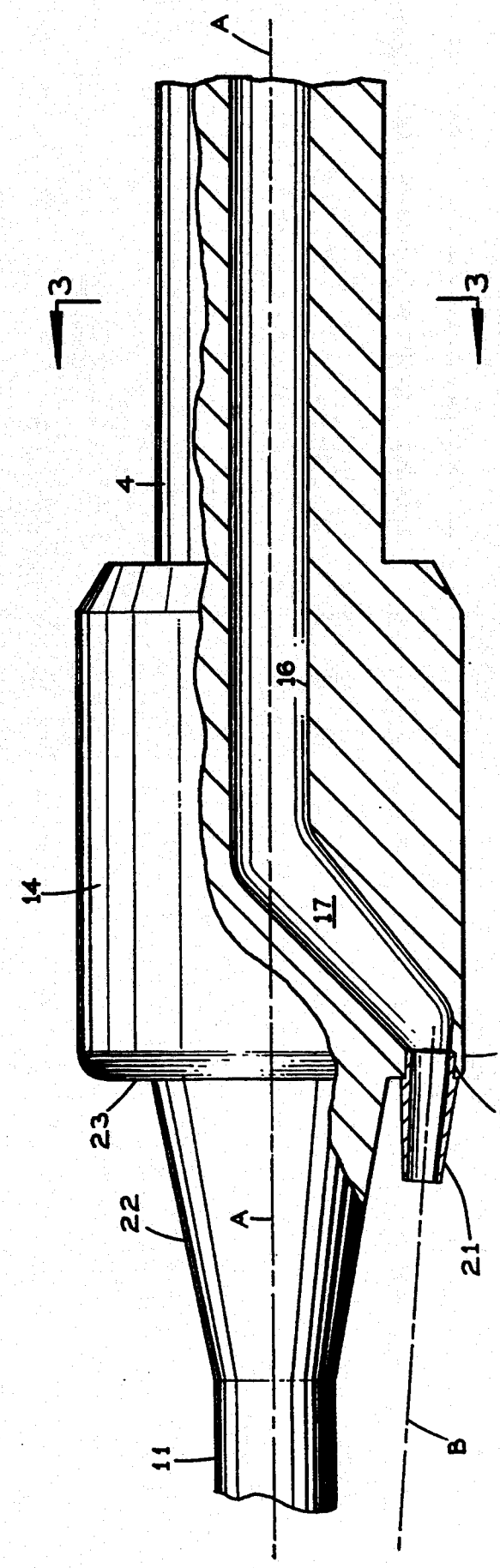

DENTAL BUR WITH LIQUID-COOLED TIP

The invention relates to a dental bur adapted to be cooled with a cooling liquid, and more particularly to a water-cooled dental bur having an internal water channel terminating in a water discharge aperture directing cooling water at the tip of the bur and having a removable distal end.

BACKGROUND OF THE INVENTION

It is known that the process of drilling and cutting creates a great deal of heat where the dental cutting tool, known as a "bone bur", cuts into the bone and causes dessication of the bone. The heat generated by the bur causes dessication and destruction of the bone. It is therefore desirable to apply cooling to the bur and the bone during the drilling and cutting process. It is also desirable for the bur to have a readily removable distal end so that the cutting tip can be inexpensively replaced when worn.

It is known from the prior art to provide a water channel in a dental bur, as shown in U.S. Pat. No. 3,393,452, which shows a dental bur having a bore through its shank and through the cutting tip of the bur extending to its distal end for admitting cooling water to the area of the tooth being drilled or cut. This arrangement, however, has the drawback that it cannot be applied to dental burs of very small diameter, such as for example 1.3 mm or less, since practical technology is not available for forming a long bore of such a small diameter. Burs of such small diameter are often required for drilling and cutting teeth. U.S. Pat. No. 5,100,322 shows a water-cooled dental tool which has an internal hollow space and holes cut transversely through the cutting tip of the tool for admitting a stream of liquid or air for cooling the drilling operation. The dental bur according to the last mentioned patent relies on only cooling liquid sprayed against the exterior of the cutting tool. The holes in the tool are, however, easily filled with cutting material from the tooth, so that the cooling action is lost.

It is accordingly an object of the present invention to provide a liquid-cooled dental bur which does not have the drawbacks of the known dental burs, and which provides effective cooling also for dental burs of quite small diameters.

It is a further object of the present invention to provide such a bur in which the cutting tip is easily removed and replaced.

Further objects and advantages of this invention will be apparent from the following detailed description of a presently preferred embodiment which is illustrated schematically in the accompanying drawings.

SUMMARY OF THE INVENTION

According to the invention, there is provided an elongated liquid-cooled dental bur having a long direction, a proximal part adapted to be inserted into a drive device connected with a source of cooling fluid, a distal part having a cutting tip, a channel in the proximal part fluidly communicating with the source of cooling fluid and at least one orifice extending from the channel directed at the cutting tip for directing a spray of cooling liquid at the cutting tip, and further including a collar radially extending from the proximal part having a circumference, wherein the orifice is disposed in the collar proximal to the circumference, and wherein the collar has an end surface disposed transversely to the long direction facing the distal part, and the orifice is disposed in the end surface.

According to a further feature the proximal end part is shaped as an elongate cylinder, and the channel is shaped as a central bore in the cylinder and the proximal end part has a facet substantially parallel with the long direction for rotationally locking the bur in the drive device.

According to still another feature, the end part has a radial recess for axially locking the bur in the drive device, and the bur tip has a diameter perpendicular to the long direction no greater than 1.3 mm.

As a still further feature, the cooling fluid is composed substantially of water.

As still another feature, the distal end of the bur is fit into an axial port in the body of the bur and removably secured with a set screw to make the cutting tip readily replaceable. The cutting tip may be substantially spherically shaped.

BRIEF DESCRIPTION OF THE DRAWINGS

FIG. 1 is a diagrammatic, part cross-sectional view of a dental bur according to the invention;

FIG. 2 is a fragmentary, part cross-sectional view of the central part of the dental bur according to the invention;

Figure 3:
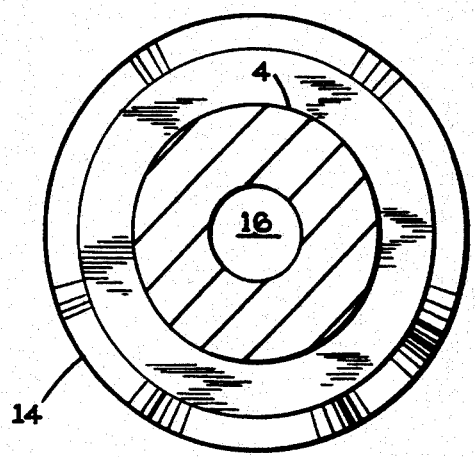
FIG. 3 is a cross-sectional view seen along the line 3—3 of FIG. 2.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

DESCRIPTION OF THE PREFERRED EMBODIMENTS

In FIG. 1 a dental bur generally at 1 is shown inserted in a drive device, generally at 2, shown in phantom lines. The drive device has an internal central channel 3 which leads to a source of cooling liquid under a given amount of pressure.

The dental bur 1 is elongated in a long direction indicated by a dash-dot line A, and is composed of a proximal part 4 and a distal end 11 having a cutting tip 12 no more than 1.3 mm in diameter with abrasive or cutting surfaces. The proximal part is insertable in a drive device 2, and has at its end 6 a facet 7, which is substantially parallel with the long direction A. The facet 7 mates with a corresponding flat surface in drive device 2 to provide a rotational lock on the bur 1.

The proximal part 6 also has an indentation or groove 8 which mates with a releasable latch 9 in the drive device 2, and provides axial lock of the dental bur. The middle proximal part 4 is advantageously of cylindrical shape in which case the dash-dot line A indicates the axis of the bur 1.

The middle proximal part 4 expands at its end 13 facing away from the drive device 2 into a collar 14 at a somewhat greater diameter of the proximal part 4. The proximal part 4 has an internal bore or channel 16 which communicates at its proximal end with the central channel 3 of the drive device 2. The channel 16 extends through the collar 14 and deviates in the collar away from the axis A via a short channel section 17 to communicate with an orifice 18 disposed proximal to the circumference 19 of the collar 14, which in turn communicates with a small spout or jet 21 which has an axis shown by the dash-dot line B, that is converging with the axis A at a point near the cutting tip 12, so as to direct a stream of cooling fluid ejected from the jet 21 at the cutting tip and the cutting area of the tooth being cut.

FIG. 2 shows in a cross-sectional enlarged view the details described above, including the channel 16 in the proximal part 4 and the collar 14, which deviates as channel section 17 and communicates with the orifice 18 and the jet 21.

FIG. 3 is an end view taken along line 3—3 of FIG. 2, showing the circumference of the collar 14, the proximal part 4 in cross-section and the internal channel 16 of the proximal part 4.

Figure 4:
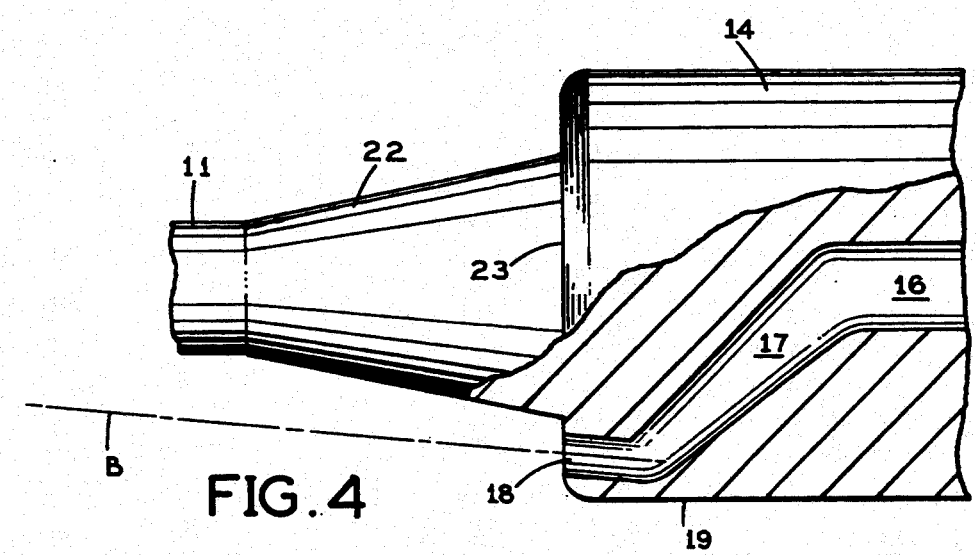
FIG. 4 is a fragmentary cross-section of the bur showing the area of the fluid aperture.

FIG. 4 shows an embodiment wherein the orifice 18 has been arranged so that it has a shape and direction that directs a stream of cooling water directly at the cutting head without the use of an intervening jet 21, as shown in FIG. 2. It follows that more than one orifice 18 may be provided, in which case the orifices are arranged equidistantly about the circumference of the collar 14. FIG. 4 also shows the collar 14 extending beyond the root 22 of the distal part 11, forming a shoulder 23 which lies in a plane perpendicular to the axis A, facing the cutting tip 12 of the dental bur. The root 22 is advantageously formed as a conical or flared part of the distal part 11.

Figure 5:
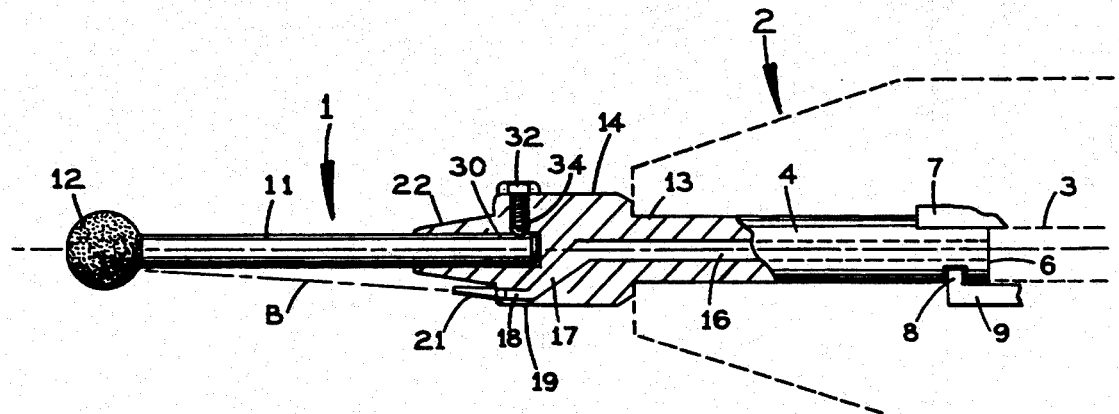
FIG. 5 is a diagrammatic, part cross-sectional view of a dental bur according to the invention, illustrating how the bur distal end is preferably removably secured in the body of the bur with a set screw and the preferred spherical cutting tip.

FIG. 5 shows a preferred embodiment of cutting tip 12 which presents a substantially spherical working outer surface 26. Distal part 11 is preferably removably secured in an axial port 30 in collar 14 with a set screw 32. Set screw 32 preferably extends through a threaded, lateral set screw bore 34 in collar 14. This feature permits replacement of a worn cutting tip 12, without the expense of replacing the entire bur 1 and its internal fluid channels 16 and 17. It is to be understood that cutting tip 12 alternatively may be separated at any point between collar 14 and cutting tip 12, and removably connected with well known means. The replaceable cutting tip may alternatively have a cylindrical shape as in FIG. 1.

I claim:

1. An elongated liquid-cooled dental bur having a long direction comprising a proximal part adapted to be inserted into a drive device connected with a source of cooling fluid, a distal part having a cutting tip, a first channel in said proximal part fluidly communicating with said source of cooling fluid, at least one orifice extending from said first channel directed at said cutting tip for directing a spray of cooling liquid at said cutting tip, a collar radially extending from said proximal part having a circumference, wherein said orifice is disposed in said collar proximal to said circumference.

2. A liquid-cooled dental bur according to claim 1, wherein said collar has an end surface disposed transversely to said long direction and facing said distal part, and said orifice is disposed in said end surface.

3. A liquid-cooled dental bur according to claim 1, wherein said proximal part is shaped as an elongate cylinder, and said first channel is shaped as a central bore in said cylinder.

4. A liquid-cooled dental bur according to claim 3, wherein said proximal part has a facet substantially parallel with said long direction for rotationally locking said bur in said drive device.

5. A liquid-cooled dental bur according to claim 3, wherein said proximal part has a radial recess for axially locking said bur in said drive device.

6. A liquid-cooled dental bur according to claim 1, wherein said bur tip has a diameter no greater than 1.3 mm.

7. A liquid-cooled dental bur according to claim 1, wherein said cooling fluid is composed substantially of water.

8. A liquid-cooled dental bur according to claim 1, wherein at least part of said distal part is removably secured to said proximal part, for removal and replacement of worn cutting tips.

9. A liquid-cooled dental bur according to claim 1, wherein said distal part is removably secured to said collar, for removal and replacement of worn cutting tips.

10. A liquid-cooled dental bur according to claim 9, wherein said distal part fits into an axial bore in said collar and is secured in said axial bore with set screw means.

11. A liquid-cooled dental bur according to claim 1, wherein said cutting tip is substantially spherically shaped.

12. A liquid-cooled dental bur according to claim 10 wherein said cutting tip is cylindrical.

13. A liquid-cooled dental bur according to claim 10 wherein said cutting tip is substantially spherical.

14. An elongated liquid-cooled dental bur having a long direction comprising a proximal part adapted to be inserted into a drive device connected with a source of cooling fluid, a distal part having a cutting tip, a first channel in said proximal part fluidly communicating with said source of cooling fluid, at least one orifice opening from said first channel and directed at said cutting tip for directing a spray of cooling liquid at said cutting tip, an expanded portion radially extending from said proximal part having a circumference, wherein said orifice is disposed in said expanded portion proximal to said circumference.

15. An elongated liquid-cooled dental bur having a long direction comprising a proximal part having a proximal part longitudinal axis and adapted to be inserted into a drive device connected with a source of cooling fluid, a distal part having a distal part longitudinal axis, an average radius and a cutting tip, a first channel in said proximal part fluidly communicating with said source of cooling fluid, said first channel having a longitudinal channel segment substantially parallel with said proximal part longitudinal axis and a lateral channel segment extending generally radially beyond said average radius of said distal part through a lateral channel containing structure, at least one orifice opening out of said lateral containing structure and directed substantially toward said distal part longitudinal axis for directing a spray of cooling liquid generally toward said cutting tip.

* * * * *